United States Patent [19]
Getz

[11] Patent Number: 5,102,335
[45] Date of Patent: Apr. 7, 1992

[54] FULL ARCH IMPRESSION AND CHECKBITE FRAME

[76] Inventor: Edwin H. Getz, 60 Olive Pl., Forest Hills, N.Y. 11375

[21] Appl. No.: 687,575

[22] Filed: Apr. 19, 1991

[51] Int. Cl.$^5$ ................................ A61C 9/00
[52] U.S. Cl. ...................................... 433/38
[58] Field of Search .............. 433/37, 38, 41, 42, 433/44, 45, 46, 47

[56] References Cited

U.S. PATENT DOCUMENTS

| 1,369,171 | 2/1921 | Graham | 433/42 |
| 2,583,170 | 1/1952 | Getz | 433/38 |
| 2,703,452 | 3/1955 | Getz | 433/42 |
| 3,250,004 | 5/1966 | Jores | 433/38 |
| 3,468,029 | 9/1969 | Moore | 433/42 |
| 4,003,132 | 1/1977 | Beck | 433/42 |
| 4,204,323 | 5/1980 | Neubert et al. | 433/38 |
| 4,689,010 | 8/1987 | Wolfe | 433/38 |

Primary Examiner—Cary E. O'Connor
Attorney, Agent, or Firm—Arthur T. Fattibene; Paul A. Fattibene

[57] ABSTRACT

An improved dental full arch and impression checkbite frame which includes an outer lingual arch and an inner labial arch which are each provided with a longitudinally extending slot for receiving and supporting therein a porous membrane which is adapted to form the support for the mass of impression material for making an impression, the respective slots defining an upper frame portion and a lower frame portion. The respective inner and outer arches are rigidly interconnected at their corresponding distal ends by a cross link. At the proximal end of the dental frame, there is provided a handle having offset bifurcated portions, whereby the bifurcated portions are respectively connected to the upper frame section and lower frame section. A rigid frame is thus defined that is free of any appreciable movement that can compromise the accuracy of a model or cast made thereby.

13 Claims, 2 Drawing Sheets

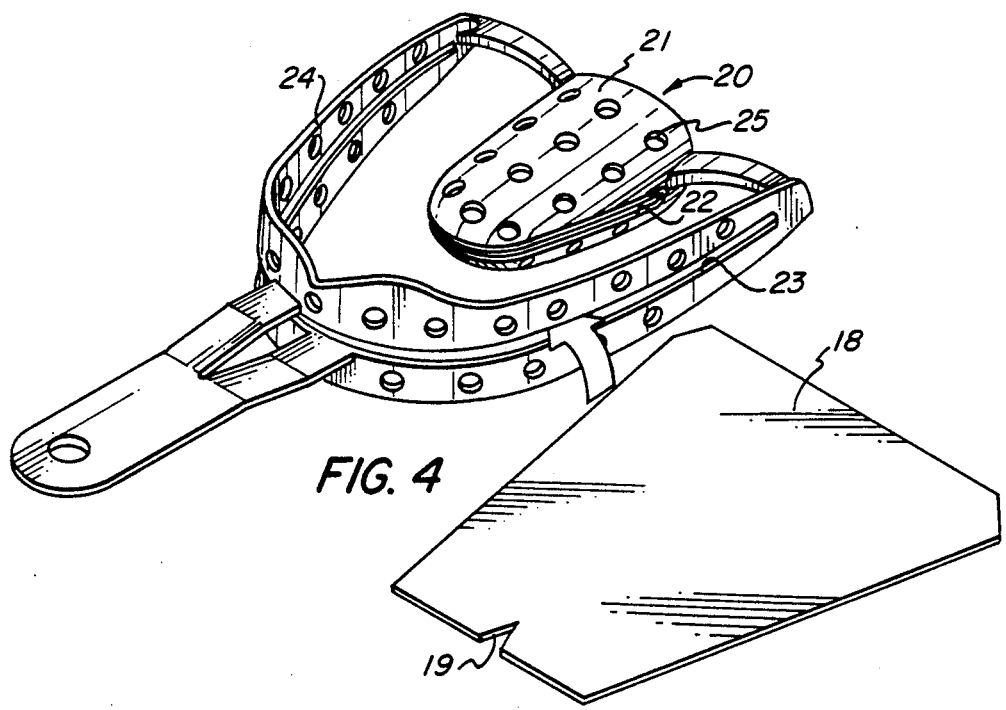
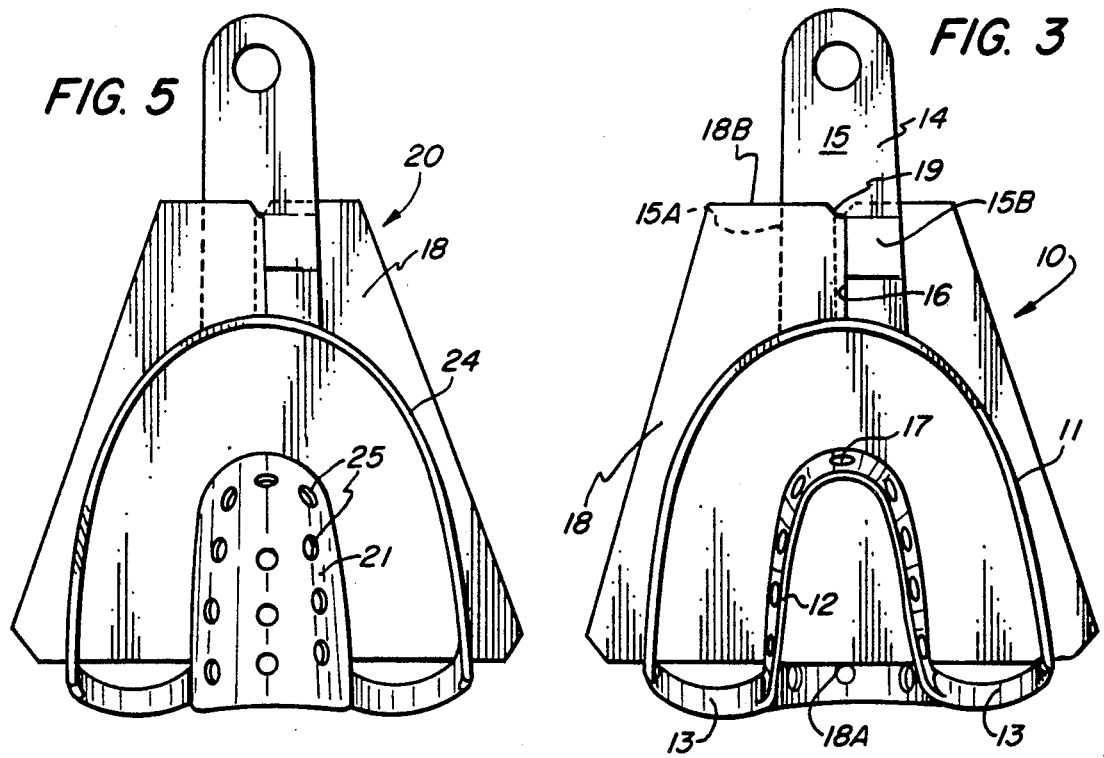

FULL ARCH IMPRESSION AND CHECKBITE FRAME

This invention is directed to a dental impression device, and more particularly to a dental full arch impression and checkbite frame.

PRIOR ART

Various dental impression devices and trays are known, and have been utilized by dentists for making impressions of patient's teeth. Some of the known dental impression devices are evidenced by U.S. Pat. Nos. 905,535; 900,541; 1,023,213; 3,250,004; 3,468,029; 4,003,132; 4,204,323 and 4,445,854, to cite a few. In addition, reference is also made to my prior U.S. Pat. Nos. 2,583,170 and 2,763,452. Despite the relatively crowded state of the art relating to dental impression devices, there exists a need for further improvements in an effort to increase or enhance the accuracy of the mold or cast formed by such impression devices. Also, the need exists to provide a relatively simply constructed impression device which is relatively simply to make and positive in operation, so as to achieve the maximum optimal results.

OBJECTS

An object of this invention is to provide an improved full arch impression and checkbite frame, which is formed as a rigid integral construction that will resist deflection by even relatively small amounts so as to insure greater accuracy in the mold or cast made thereby.

Another object is to provide for a full arch impression and checkbite frame arranged for supporting the mass of impression material in which maxillary and mandibular impression material are integrally bonded.

Another object is to provide a full arch impression and checkbite frame having inner and outer arches defining an upper and lower frame section which are rigidly connected.

Another object is to provide a full arch impression and checkbite frame having a novel handle construction for facilitating the use thereof.

SUMMARY OF THE INVENTION

The foregoing objects and other features and advantages are attained by a full arch impression and checkbite frame that includes an outer lingual arch and an inner labial arch which are integrally interconnected at their respective distal ends by a cross-link. Each of the respective arches are provided with an elongated slot formed intermediate the width of the respective arch and which terminates short of the distal ends thereof. The slots thus define an upper frame section and a lower frame section. Connected to the proximal end of the frame is a handle having its connected end bifurcated, whereby the bifurcated ends are laterally offset with one of the bifurcated ends being connected to the upper frame portion of the outer arch and the other bifurcated portion connected to the lower frame section of the outer arch. A porous or open mesh membrane is inserted into the slots to form a partition to which the impression material is applied, for simultaneously making the maxillary and mandibular impressions of one's bite. The respective arches may be provided with a series of holes or openings therein to facilitate the bonding of the impression material thereto. Also, if desired, an inner arch may be formed with a roof or vault.

FEATURES

A feature of this invention resides in the provision that the respective arches are rigidly connected at their respective distal ends to provide a complete circumferential rigid support about the distal arches.

Another feature resides in the provision of a handle that supports and stabilizes the separated and divided upper and lower portions of the outer arch at a position above and below the slot.

Another feature resides in the provision whereby the membrane can be maintained within the frame in a 3-point triad manner.

Another feature resides in the provision that the bifurcated handle allows for locking in place the membrane insert.

Other features and advantages will become more readily apparent when considered in view of the specification and drawings in which:

FIG. 3 is a top plan view of the dental frame of FIG. 2.

FIG. 4 is an exploded perspective view of a modified form of the invention.

FIG. 5 is a top plan view of the assembled embodiment of FIG. 4.

DETAIL DESCRIPTION

Figure 2:
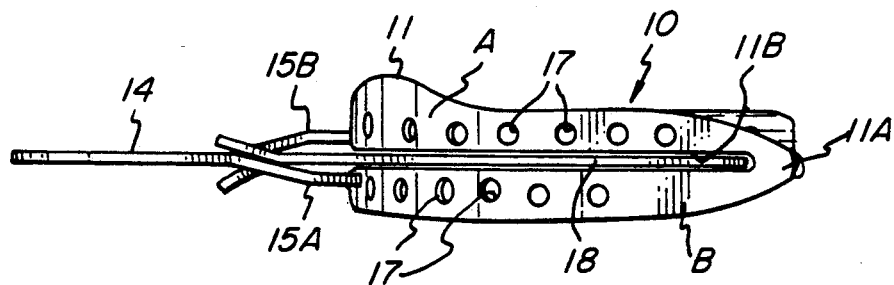
FIG. 2 is a side elevation view of the embodiment of FIG. 1 with the membrane in place.
Figure 1:
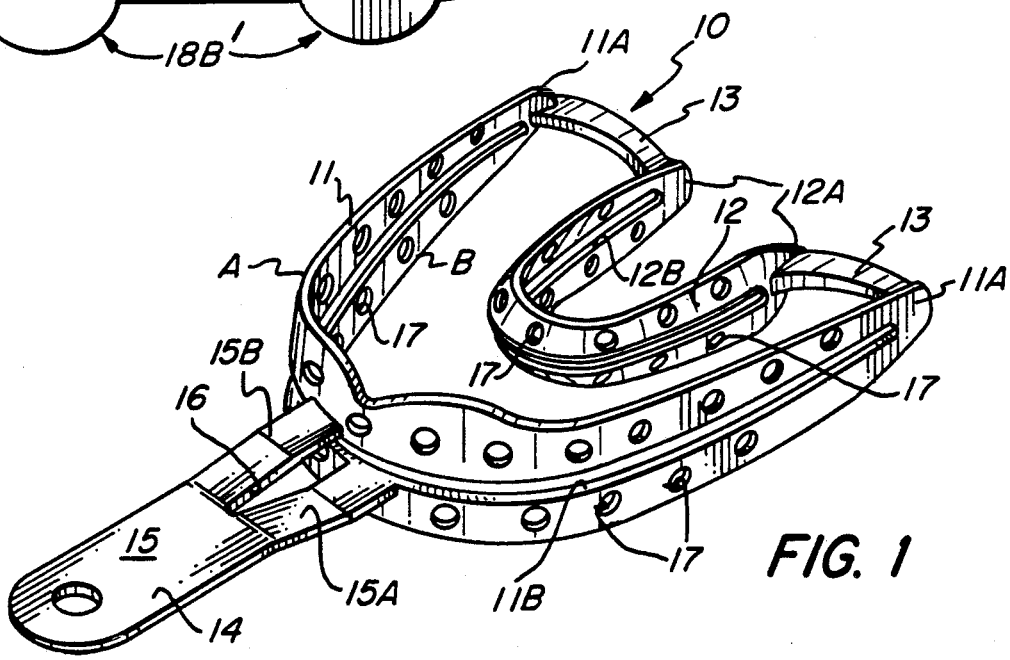
FIG. 1 is a perspective view of a full arch impression and checkbite frame embodying the invention without the membrane.

Referring to the drawings, there is shown in FIGS. 1 to 3 an illustrated embodiment of the invention. As shown therein, the full arch impression and checkbite frame 10 form an outer or lingual arch 11 shaped to accommodate the full complement of a patient's bite or teeth. A complementary inner or labial arch 12 is spaced inwardly therefrom. As best seen in FIG. 1, the outer or lingual arch 11 is formed as a generally flat strip of rigid metallic material, e.g. stainless steel, in which the width of the strip is disposed in a vertical plane. The respective corresponding distal ends 11A and 12A are rigidly interconnected by a rigid cross link or connecting member 13. It will be understood that the cross link or connecting member 13 may be slightly bowed as shown, or more curved, or may comprise a straight tie bar connected between the distal ends 11A, 12A of the inner and outer arches 11 and 12.

Each of the respective arches 11 and 12 is provided with a longitudinally extending slot 11B and 12B respectively. As shown, each of the slots 11B and 12B extend along the medial portion of the respective arches and each slot 11B and 12B terminates at a point spaced from the distal ends 11A and 12A of the respective arches 11 and 12. The slots 11B and 12B define a separation in the respective arches 11 and 12 to define an upper frame section A and a lower frame section B. it will be understood that slots 11B and 12B of the respective arches 11 and 12 are disposed in a common horizontal plane.

Connected to the proximal end of the outer arch 12 is a handle means 14. As shown, the handle means 14 comprises a metal plate which is bifurcated at its connecting end as indicated at 16. The bifurcation thus defines two leg portions 15A, 15B, which are vertically offset whereby the free end of leg portion 15A is connected to the lower portion B of the outer arch 12, and the other leg portion 15 is rigidly connected to the upper portion A of the outer arch 11. Thus, it will be noted that the ends of the leg portions 15A and 15B are disposed to either side of the slot 11B formed in arch 11, for reasons as will be hereinafter set forth. From the construction described, it will be noted that the respective arches and 12 are rigidly connected at their corresponding distal ends by a cross-link 13 and the upper and lower frame portions A and B are rigidly interconnected at their proximal end by means of the bifurcated handle construction described. The arrangement is such that the frame described is integrally formed so as to resist deflection which can adversely affect the mold or casting by an impression. The rigidity of the frame described can be further enhanced by providing a slight arc or bow in the vertical plane of the inner arch as shown in FIG. 1. If desired, the upper and lower frame portions A and B, formed by the respective arches 11 and 12, may be provided with a series of openings 17 extending therethrough.

A porous or open mesh membrane 18 is inserted through the corresponding slots 11A and 12A of the respective arches 11 and 12 to define a partition or separation between the upper and lower frame sections A and B. As best seen in FIG. 3, the membrane 18 is formed in the shape of a trapezoid in which the distal end 18A is wider than the proximal end 18B. Intermediate the width of the proximal end 18B, there is provided a notch 19 which functions to stabilize the positioning of the membrane by centering of the notch 19 with the end of the bifurcate 16. In the arrangement described, the membrane functions as a free floating member that is loosely supported in the slots 11A and 11B to divide the frame into a maxillary or upper section A and a mandibular or lower section B. The membrane is free to move as it is retained in a relatively neutral position by its shape and size as related to the shape and size of the slots. The membrane thus divides the impression mass or material applied thereto into an upper and lower part. Since the porous or open mesh receives the impression material in its pores or openings, there is formed a positive bond between the membrane and the upper and lower impression masses. Accordingly, the impression material becomes the primary stabilizer for the membrane; and keeps it in place better than the frame through which it passes.

Figure 6:
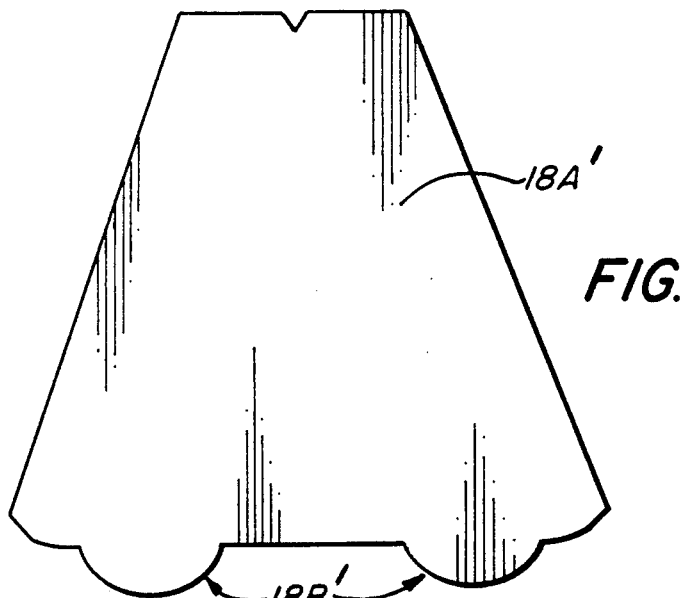
FIG. 6 is a plan view of a modified membrane.

It will be understood that the membrane may assume other shapes and/or be provided with projecting tabs. FIG. 6 illustrates such modified construction. As shown, the membrane 18A' of FIG. 6 differs slightly, in that distal tabs 18B' are provided. FIGS. 4 and 5 illustrate a modified impression frame 20. This form of the invention is similar to that herein described, with the exception that the inner or labial arch is defined as a vault or roof 21 having an elongated slot 22 co-planar disposed with respect to slot 23 of the outer arch 24. As shown, the roof or vault 21 is also provided with openings 25. In all other respects, the construction, operation, and function of the embodiment of FIGS. 4 and 5 are similar to that of FIGS. 1 to 3.

While the invention has been described with respect to particular embodiments thereof, it will be understood and appreciated that variations and modifications may be made without departing from the spirit and scope of the invention.

What is claimed is:

1. A full arch impression and checkbite frame comprising:
   an outer lingual arch and an inner labial arch,
   said lingual and labial arches each having a distal end portion and a proximal end portion,
   means interconnecting said lingual and labial arches together at their distal end portions,
   each of said lingual and labial arches having a longitudinally extending slot formed therein to define an upper arch portion and a lower arch portion,
   said slots formed in said lingual and labial arches being disposed in a common plane extending transversely thereof,
   a handle means connected to the proximal end of said lingual arch,
   said handle means being bifurcated at its connecting end to said lingual arch to define a pair of off-set leg portions,
   one of said pair of off-set leg portions being connected to said upper portion of said lingual arch and the other of said offset leg portions being connected to said lower portion of said lingual arch,
   and a membrane inserted into said slots forming a partition between said upper and lower portions of said arches, said membrane being adapted to support the impression material on either side thereof.

2. A full arch impression and checkbite frame as defined in claim 1, wherein each of said arches are provided with a series of holes extending therethrough, said holes being disposed above and below said slots.

3. A full arch impression and checkbite frame as defined in claim 1, wherein said membrane includes a distal end and a proximal end having a notch at the proximal end intermediate the width thereof so that the proximal end of said membrane projects forwardly of said bifurcate of said handle means.

4. A full arch impression and checkbite frame as defined in claim wherein said inner arch having a vault extending transversely thereof, said inner arch slot partitioning said vault into an upper and lower vault portion.

5. A full arch impression and checkbite frame as defined in claim 1, wherein said interconnecting means comprises a cross link interconnecting the corresponding distal end portions of said inner and outer arches; said cross pieces being disposed below said membrane.

6. A full arch impression and checkbite frame as defined in claim 1, wherein said membrane is porous which allows the impression material to flow through said porous membrane to form a positive bond therewith and between the upper and lower masses of impression material disposed thereon for making a full bite impression.

7. A full arch impression and checkbite frame as defined in claim 1, wherein said membrane is trapezoidal in shape.

8. A full arch impression and checkbite frame as defined in claim 1, wherein said frame is formed of rigid metal.

9. A full arch impression and checkbite frame comprising:
   an inner and outer U-shaped arch forming means,
   said inner and outer arch forming means having a distal end portion and a proximal end portion,
   a longitudinal slot formed in each of said inner and outer arch forming means to define each of said arch forming means into an upper frame section and a lower frame section, said slots terminating short of the distal end portion of the respective arch forming means, whereby said upper and lower frame sections of the respective arch forming means define a unitary member, means for rigidly interconnecting the distal end portion of said inner and outer arch forming means together, and a handle means fixedly interconnecting the upper and lower frame sections together at the proximal end of said outer arch forming means to prohibit any relative pivoting of the upper frame section from the lower frame section.

10. A full arch impression and checkbite frame comprising:

an inner and outer, spaced apart, arch forming means, said arch forming means having a distal end portion and a proximal end portion, a longitudinal slot formed in each of said inner and outer arch forming means to define said arch forming means into an upper frame section and a lower frame section, said slots terminating adjacent to the distal end of the respective arch forming means, means for rigidly interconnecting the distal ends of said inner and outer arch forming means together, and a handle means interconnecting the upper and lower frame sections together at the proximal end of said outer arch forming means, said handle means having a connecting end, said connecting end being bifurcated to define offset leg portions, one of said leg portions being connected to said upper frame section and the other leg portion being connected to the lower frame section at the proximal end thereof.

11. A full arch impression and checkbite frame as defined in claim 10, and including a porous membrane inserted and supported in said slots.

12. A full arch impression and checkbite frame as defined in claim 10, wherein said upper frame section and lower frame section are provided with a series of holes formed therein, and said arch forming means are made of a rigid metal.

13. A full arch impression and checkbite frame as defined in claim 10, wherein said inner arch forming means includes a vault disposed below and above its respective slot.

* * * * *